(12) United States Patent
Hansen et al.

(10) Patent No.: US 9,149,385 B2
(45) Date of Patent: Oct. 6, 2015

(54) URINE MEASURING VESSEL AND HOSE CONNECTION

(75) Inventors: Trygve Kalf Hansen, Jyllinge (DK); Michael James, Elkesley (GB)

(73) Assignee: UNOMEDICAL A/S, Birkerod (DK)

( * ) Notice: Subject to any disclaimer, the term of this patent is extended or adjusted under 35 U.S.C. 154(b) by 1355 days.

(21) Appl. No.: 12/602,305

(22) PCT Filed: Jun. 1, 2007

(86) PCT No.: PCT/DK2007/050065
§ 371 (c)(1), (2), (4) Date: Apr. 26, 2010

(87) PCT Pub. No.: WO2008/145123
PCT Pub. Date: Dec. 4, 2008

(65) Prior Publication Data
US 2010/0210969 A1 Aug. 19, 2010

(51) Int. Cl.
*A61B 5/20* (2006.01)
*A61F 5/44* (2006.01)

(52) U.S. Cl.
CPC ............... *A61F 5/44* (2013.01); *A61F 5/4404* (2013.01)

(58) Field of Classification Search
CPC .................................. A61F 5/4404; A61F 5/44
USPC ........ 600/573, 574, 580, 581; 4/144.1–144.4; 604/318, 322, 326
See application file for complete search history.

(56) References Cited

U.S. PATENT DOCUMENTS

| | | | |
|---|---|---|---|
| 2,198,922 A | | 4/1940 | Shaw |
| 2,591,208 A | | 4/1952 | Seymour et al. |
| RE26,674 E | * | 9/1969 | Ilg .................................. 222/570 |
| 3,736,934 A | * | 6/1973 | Hennessy ..................... 604/342 |
| 3,781,922 A | * | 1/1974 | Ericson .......................... 4/144.1 |
| 3,835,857 A | | 9/1974 | Rogers, III et al. |
| 3,901,235 A | * | 8/1975 | Patel et al. .................... 604/323 |
| 4,178,934 A | | 12/1979 | Forman |
| 4,265,118 A | | 5/1981 | Griesel |
| 4,319,573 A | | 3/1982 | Whitlock |
| 4,579,126 A | | 4/1986 | Cianci |
| 4,625,734 A | | 12/1986 | Sherlock |
| 4,758,023 A | | 7/1988 | Vermillion |

(Continued)

FOREIGN PATENT DOCUMENTS

| | | |
|---|---|---|
| DE | 29818311 | 1/1999 |
| EP | 0471413 | 2/1992 |

(Continued)

*Primary Examiner* — Sean Dougherty
*Assistant Examiner* — Michael C Stout
(74) *Attorney, Agent, or Firm* — Wilson Sonsini Goodrich & Rosati

(57) ABSTRACT

A hose connection for an arrangement for collection of liquid from a patient is disclosed which connection comprises a first tubular member (1) to be in fluid connection with the patient and having one or more protrusions (3) arranged on an outer surface, and an outlet (2), and further comprises a collection bag (24) having an inlet to be connected to the outlet for collection of liquid coming through the first tubular member. The inlet comprises a second tubular member (5) being connected to the bag and adapted to receive and surround at least a part of said first tubular member. The second tubular member has one or more receiving means (6, 11) being engageable with the protrusions for providing a locked, but separable connection between the first and second tubular member.

13 Claims, 14 Drawing Sheets

(56) References Cited

U.S. PATENT DOCUMENTS

| | | | |
|---|---|---|---|
| 4,846,798 A * | 7/1989 | Holtermann et al. | 604/339 |
| 4,889,532 A * | 12/1989 | Metz et al. | 604/330 |
| 4,925,216 A * | 5/1990 | Steer | 285/3 |
| 4,929,245 A * | 5/1990 | Holtermann et al. | 604/338 |
| 4,936,837 A * | 6/1990 | Wexler et al. | 604/326 |
| 5,071,413 A * | 12/1991 | Utterberg | 604/533 |
| 5,090,408 A * | 2/1992 | Spofford et al. | 128/207.14 |
| 5,356,396 A | 10/1994 | Wyatt et al. | |
| 5,685,875 A * | 11/1997 | Hlavinka et al. | 604/409 |
| 5,785,044 A * | 7/1998 | Meador et al. | 600/573 |
| 5,810,768 A * | 9/1998 | Lopez | 604/500 |
| 5,842,233 A * | 12/1998 | Broden | 4/144.1 |
| 6,083,207 A * | 7/2000 | Heck | 604/256 |
| 6,098,210 A * | 8/2000 | Broden | 4/144.1 |
| D464,729 S * | 10/2002 | Rehrig | D24/122 |
| 6,482,190 B1 | 11/2002 | Genese | |
| D467,338 S * | 12/2002 | Rehrig | D24/122 |
| 6,592,544 B1 * | 7/2003 | Mooney et al. | 604/43 |
| 6,684,414 B1 * | 2/2004 | Rehrig | 4/144.1 |
| 7,087,042 B2 * | 8/2006 | Montgomery | 604/342 |
| 7,140,509 B2 * | 11/2006 | Yang | 220/709 |
| 7,802,824 B2 * | 9/2010 | Christensen et al. | 285/399 |
| 7,824,393 B2 * | 11/2010 | Fangrow | 604/533 |
| 2002/0123739 A1 | 9/2002 | Haacke et al. | |
| 2004/0087906 A1 * | 5/2004 | Henderson et al. | 604/187 |
| 2004/0215158 A1 | 10/2004 | Anderson | |
| 2004/0267159 A1 * | 12/2004 | Yong et al. | 600/575 |
| 2005/0033269 A1 * | 2/2005 | Decaria | 604/533 |
| 2006/0074389 A1 * | 4/2006 | Montgomery | 604/332 |
| 2006/0122568 A1 | 6/2006 | Elson et al. | |
| 2006/0157981 A1 * | 7/2006 | Christensen et al. | 285/331 |
| 2006/0211999 A1 * | 9/2006 | Fangrow | 604/246 |
| 2006/0253091 A1 * | 11/2006 | Vernon | 604/353 |
| 2006/0264848 A1 * | 11/2006 | Fangrow | 604/249 |
| 2006/0264909 A1 * | 11/2006 | Fangrow | 604/539 |
| 2006/0264910 A1 * | 11/2006 | Fangrow | 604/539 |
| 2006/0270999 A1 * | 11/2006 | Fangrow | 604/249 |
| 2006/0271016 A1 * | 11/2006 | Fangrow | 604/246 |
| 2007/0010760 A1 * | 1/2007 | Rosenfeld | 600/573 |
| 2007/0088325 A1 * | 4/2007 | Fangrow, Jr. | 604/533 |
| 2007/0112312 A1 * | 5/2007 | Fangrow | 604/246 |
| 2007/0112313 A1 * | 5/2007 | Fangrow | 604/246 |
| 2007/0191777 A1 * | 8/2007 | King | 604/164.08 |
| 2007/0213639 A1 * | 9/2007 | Salvadori et al. | 600/584 |
| 2008/0287919 A1 * | 11/2008 | Kimball | 604/533 |
| 2013/0047587 A1 * | 2/2013 | Maus et al. | 60/295 |

FOREIGN PATENT DOCUMENTS

| | | |
|---|---|---|
| EP | 0633039 | 1/1995 |
| EP | 0398890 | 2/1995 |
| EP | 0901778 | 3/1999 |
| EP | 0983746 | 3/2000 |
| EP | 1820446 | 9/2009 |
| EP | 0008450 | 4/2010 |
| EP | 1820478 | 4/2010 |
| FR | 2742518 | 8/1997 |
| GB | 1222250 | 2/1971 |
| GB | 2198952 | 6/1988 |
| WO | 89/05119 | 11/1988 |
| WO | 8905119 | 6/1989 |
| WO | 91/00074 | 1/1991 |
| WO | 9608219 | 6/1995 |
| WO | 99/36009 | 7/1999 |

* cited by examiner

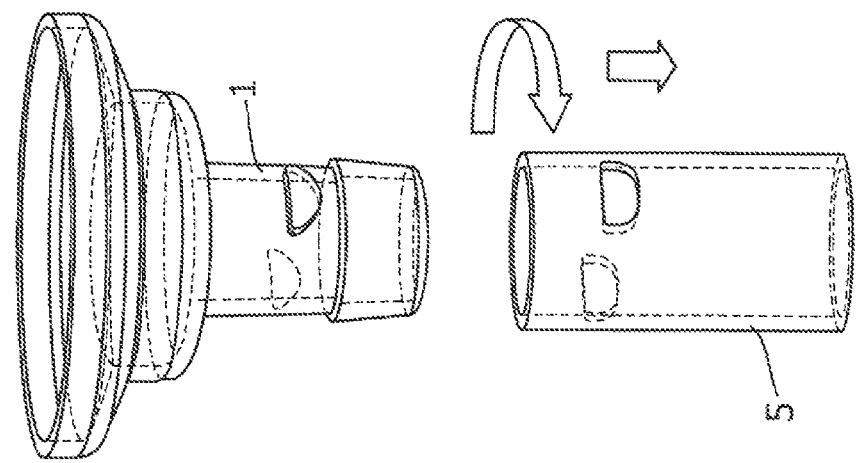
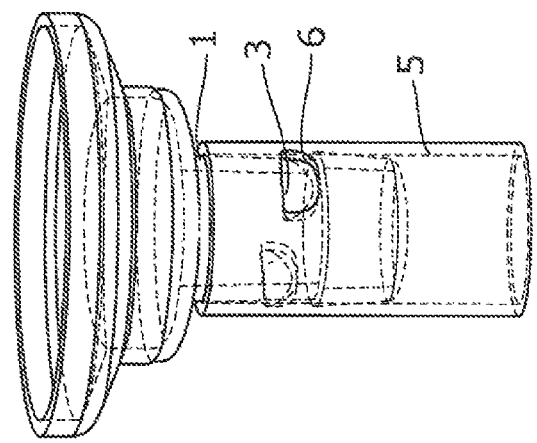
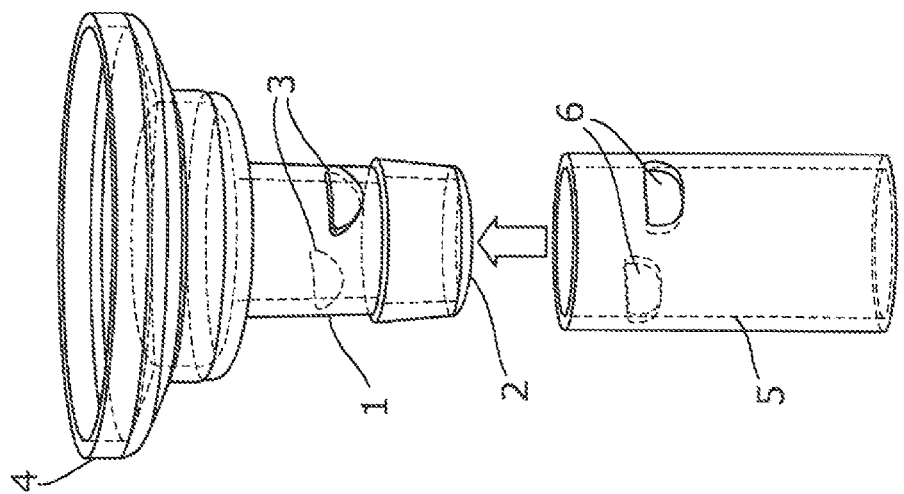

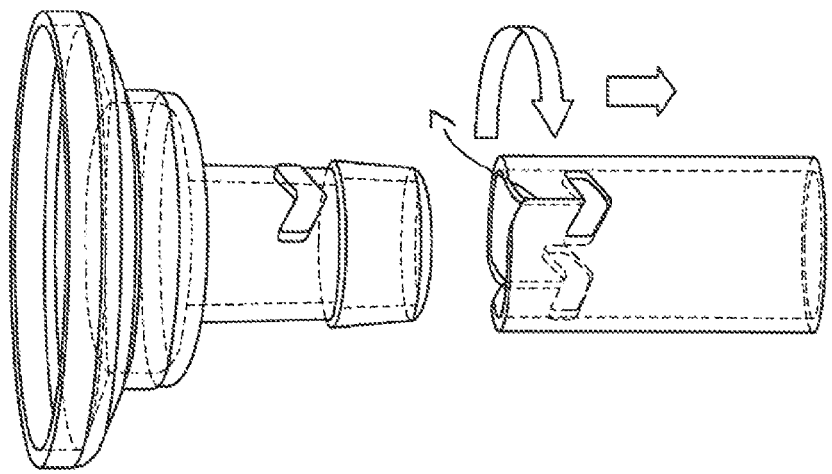
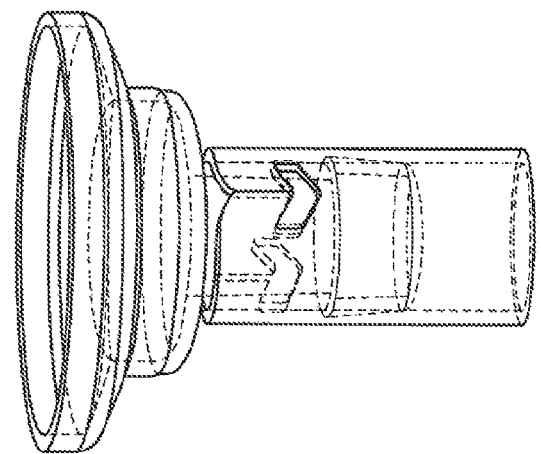
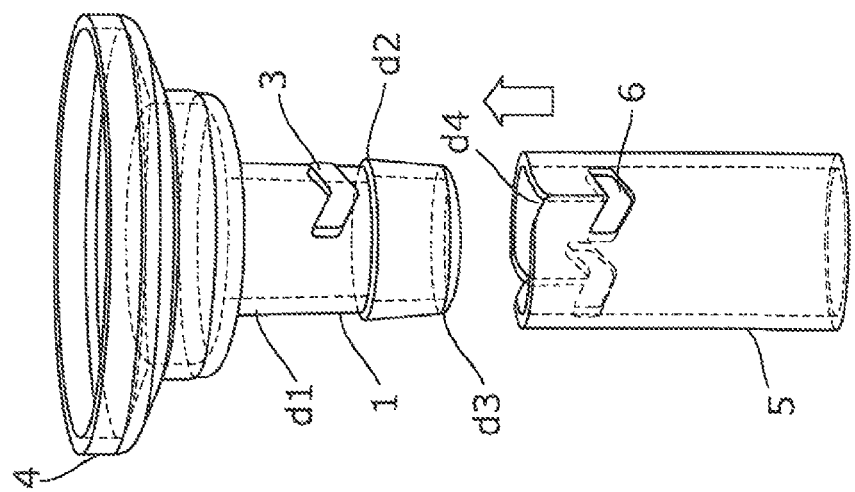

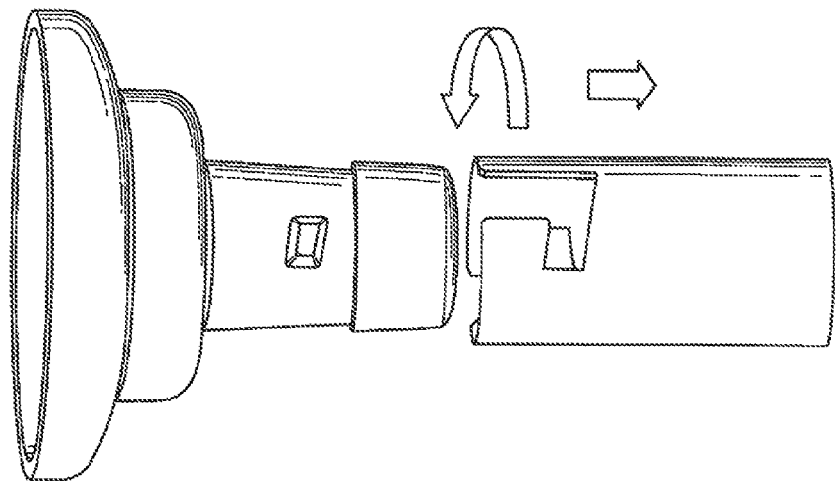
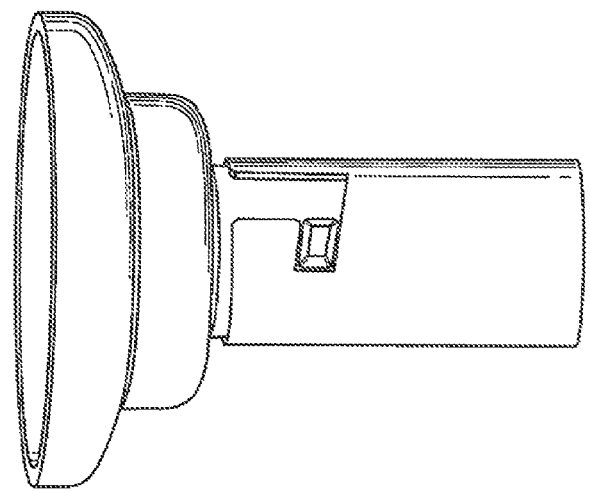
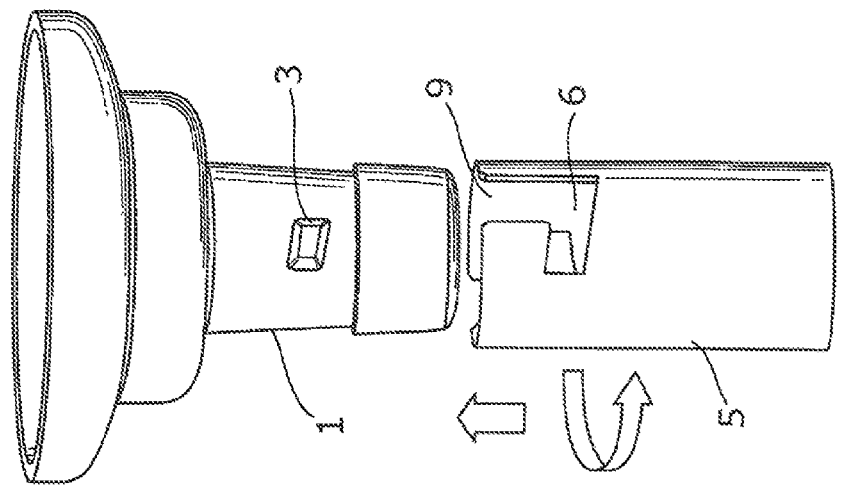

Print on bag indicates where to squeeze

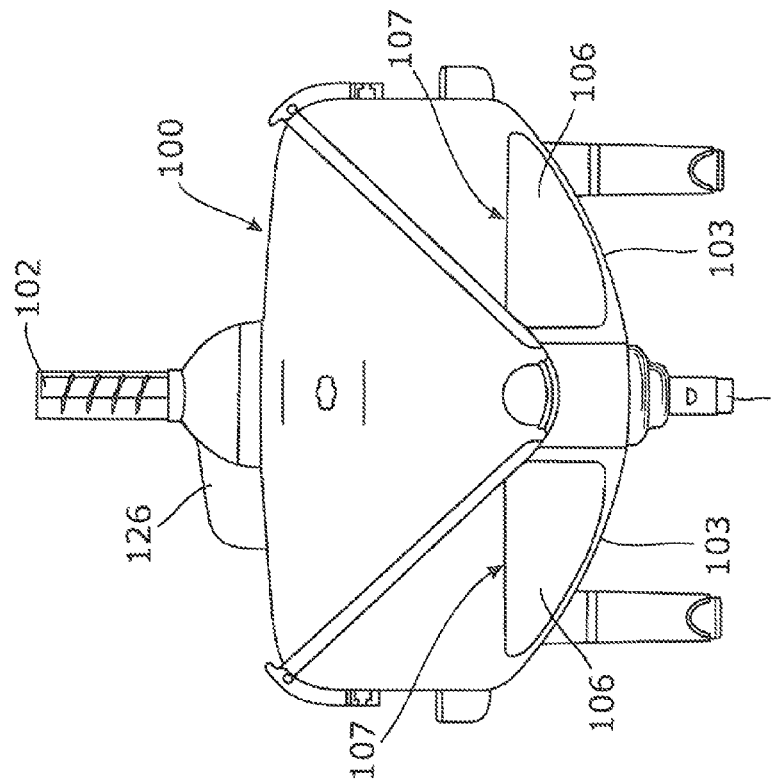
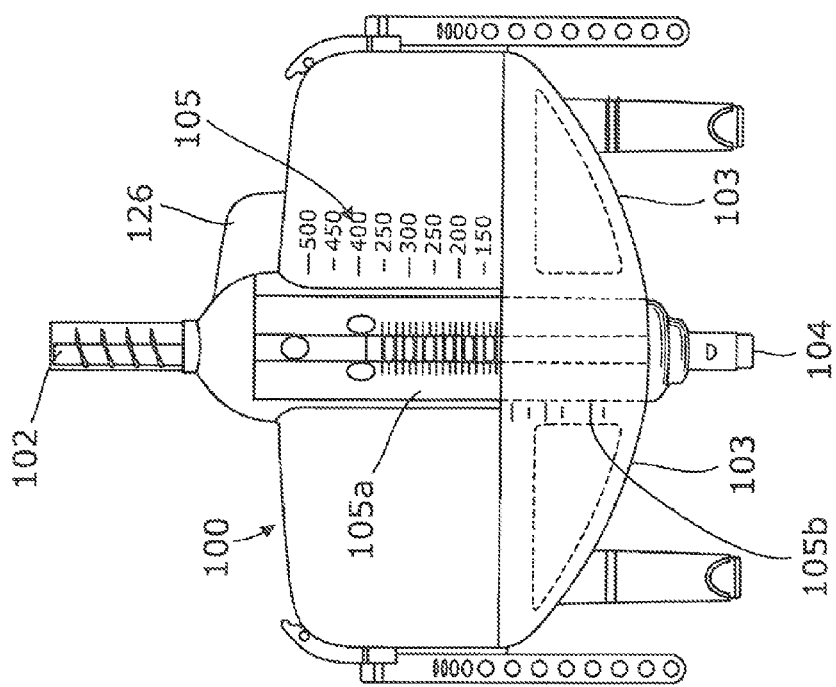

URINE MEASURING VESSEL AND HOSE CONNECTION

The present invention relates to a measuring vessel and a hose connection for an arrangement for collection of liquid from a patient. In particular, the connection may be used between a collection bag and a vessel for measuring the volume of urine from bedridden patients.

BACKGROUND OF THE INVENTION

Measurement and collection of liquid from patients at hospitals is obtained by use of a catheter inserted into the patient, e.g. into the bladder, said catheter being connected to a measuring vessel or a collection bag for collecting the liquid.

Often the vessel or catheter is fixed connected to a collection bag, which can be emptied by use of a valve in the bottom of the bag. However, it is preferable that the bag can be replaced by a new one when it is full instead of just emptying it. This replacement must be done more than once a day, and it is therefore important that it can be done fairly easily for the nurse in order to reduce his/her workload and to avoid the risk of spillage. Thus, the connection between the bag to be replaced and the other part(s) must be separable and performed without the need of much energy, but it still has to be a proper connection and be completely tight during use.

The characteristics of known hose connections are that they are either to loose and disconnect during use, or are too tight and very difficult to disconnect.

US 2004/0215158 discloses an in-line hose connector for a urinary catheter. The connector has a first part with a hose barb connected to the catheter tube and a second part with a cylindrical opening and a circumferentially extending fastening strap. A projection of the second part fits into a hole on the fastening strap after twisting the pieces and is so shaped as to aid in disengaging the fastening strap from the projection and thus disconnect the parts when a tension force is exerted.

As the connector parts of US 2004/0215158 are both made of a hard plastic, an O-ring between these parts must provide the sealing. Furthermore, the construction is very complicated and expensive as it consists of two moulded parts each having a part of a catheter tube in the end.

Another known hose connection consists of a female tube of a bag being slid over a male tube, the male tube having a plurality of conical shaped protrusions with an increasing diameter so that the male tube is connected to the female tube by means of friction provided due to the increasing diameter. Such a connection provides a good tightening, but it is very difficult to separate without using much energy and without spillage, or it may even not be separable at all.

Other hose connections are disclosed in US 2002/123739, EP 0 901 778, DE 298 18 311, U.S. Pat. No. 5,356,396, and U.S. Pat. No. 4,579,126.

It is an object of the present invention to provide a hose connection between a collection bag and the fluid connection to the patient, which connection is easy to assemble and separate, simpler and thus cheaper to manufacture, while still providing proper tightening during use.

SUMMARY OF THE INVENTION

This objective and the advantages that will become evident from the following description of the invention are obtained by the following hose connection according to a first aspect of the present invention, said hose connection for an arrangement for collection of liquid from a patient comprising;

a first tubular member to be in fluid connection with the patient and having one or more protrusions arranged on an outer surface said protrusions comprising a support surface (21) at least partly formed as a ledge, and an outlet, a collection bag having an inlet to be connected to said outlet for collection of liquid coming through said first tubular member, said inlet comprising a second tubular member being connected to the bag and adapted to receive and surround at least a part of said first tubular member, the second tubular member having one or more recesses and/or edges being engageable with said protrusions, respectively, for providing a locked, but separable connection between the first and second tubular member.

The second tubular member is preferably connected to the bag by adhesion, but it may be an integrated part of the bag, e.g. by in-moulding. The second tubular member can for example be a piece of a known soft plastic hose, e.g. of PVC, which can be adhered in a prefabricated hole in the bag, thus providing a cheap construction being easy to manufacture. As the construction is cheap to manufacture, it allows for a disposable bag that does not need be reused but can be thrown away after use.

The protrusion(s) comprise a support surface for the recess(es) or edges, which extends substantially perpendicularly and radially out from the outer surface, and an inclined surface extending from the distal end of said support surface towards the outer surface. The support surface is at least partly formed as a ledge which supports the recess(es) which preferably has a corresponding surface adapted to abut on the ledge in order to provide a safely locked connection. The ledge may be substantially level or flat or have any other suitable configuration that provides a rest which the corresponding recess(es) may engage with for preventing unintended disconnection caused by tension force.

The inclined surface provides a chute along which the tubular member can slide until the recess reaches the support surface, the chute enabling an easier connection between the two tubular members. The inclined surface may for example be convex or concave.

Preferably, the recesses go through the sidewall of the second member and have an outline substantially identical to the outline of the protrusions, such as, but not limited to, half-circle formed or arrow-formed or rectangular.

The second tubular member may comprise slot(s) providing an opening channel in the sidewall extending from an upper edge of the second member to the recess(es), so that the protrusions can be guided through the channel to obtain the engaged position in the recess(es).

The first and second tubular members may comprise two recesses and protrusions, respectively, arranged on opposite sides of each member. In an embodiment, the first tubular member comprises two protrusions arranged diametrically opposite. However, the tubular members may comprise just one or more than two recess(es) and protrusions, respectively, being evenly or unevenly distributed along the surface of the members.

The first tubular member is preferably substantially conical with an outer diameter (d3) near the outlet being smaller than an outer diameter (d1) upstream thereof, and an inner diameter (d4) of the second tubular member being preferably larger than the outer diameters (d1) and (d3) of the first tubular member. The second tubular member is thereby easy to slide onto the first tubular member without any significant friction, but will still be locked connected to the first tubular member due to the engagement between the recess(es) and protrusion(s).

In combination with the engagement between the recess(es) and protrusions, a connection is provided which is easy to assemble and separate, simple and cheap to manufacture and provides a proper tightening.

In order to obtain an even better tightening, the first tubular member may comprise an intermediate widened portion with a diameter (d2) being larger than (d1), (d3) and (d4). However, the diameter (d2) is preferably not much larger than (d4) in order to obtain the easy assembling and separation without much friction. The widened portion may be provided by a conical protrusion on the outer surface.

The diameters may for example be (d1)=11 mm, (d2)=11.4 mm, (d3)=10.8 mm, and (d4)=11.2 mm, but they can of course vary.

Preferably, the first and second tubular member have congruent cross-sectional outlines meaning that they fit smoothly into each other, and the second member preferably covers the entire outer surface of the first tubular member, but not necessarily.

In an embodiment, the protrusions are provided at a distal end of the first tubular member and are adapted to engage a distal edge of the second tubular member. In one embodiment, the first tubular member comprises at least two opposite flexible leg parts each having a protrusion (a barb) adapted to engage a distal edge of the second tubular member, the leg parts being bendable towards each other for disengaging the protrusions from the edge of the second tubular member.

The first and second tubular members can be connected by pushing and/or turning the second tubular member over the first tubular member until the protrusions engage the recesses. In the embodiment with the opening channel as mentioned above, the second tubular member is both pushed and turned in order to guide the protrusions into the recess(es). The protrusions and recesses can be disengaged from each other preferably by compressing and/or turning the second tubular member. The second tubular member is preferably made of a soft plastic material, so that it can be compressed on two opposite sides resulting in a widening of the sidewall containing the recess(es), which then will disengage the protrusions on the first tubular member.

The first and/or the second tubular members may in embodiments comprise a substantially semicircular section forming a ramp engaging with the other member for facilitating disengagement of the members by twisting them in relation to each other. Preferably it is the second tubular member that is twisted. The semicircular section forming a ramp is preferably provided so as to partly encircle a part of the first tubular member having the diameter d1 and preferably closer to the inlet end of the first tubular member than to the outlet end.

In embodiments the first and/or second tubular member may alternatively comprise an annular section at least partly forming a ramp. By at least partly is meant that the annular section may e.g. partly comprise a substantially semicircular section forming a ramp and partly an adjacent semicircular section without a ramp. However, the annular section may preferably comprise two adjacent semicircular sections provided with ramps. In principle any number of sections provided with ramps may together form the annular section. The engaging surface on the other member may in such embodiments be suitably adapted according to the section(s) on the first member.

The semicircular or annular section forming a ramp may be provided on, or as, the engaging surface of the second tubular member provided that one or more corresponding recesses are made in the outer engaging surface part of the first tubular member.

Preferably, only one of the members is provided with a semicircular or annular section but such a section may also be provided on both members.

By providing such a ramp on either one or both members according to the invention, it is particularly easy for a person to intentionally disconnect the hose connection, preferably by twisting the second tubular member in relation to the first tubular member. This is because the ramp on the section slides against the surface of the other member which in turn causes the recess(es) on the second tubular member to be released from its resting position on the ledge of the first tubular member. No excessive force will thus be necessary; the members can be released from each other in a comfortable manner without compromising a safe and tightly locked connection in use.

The first tubular member is preferably made of a hard plastic material having a Shore A value of approx. 100, such as SAN plastic. The second tubular member is preferably made of a soft plastic material having a Shore A value of approx. 80, such as poly-vinyl-chloride.

The first tubular member may be a part of a hose/catheter connected directly to an organ of a patient, or it may be a part of a measuring vessel for measuring volume of liquid, such as urine. The first tubular member may be connected to this vessel, or it may be a fixed in-moulded part of said vessel defining the outlet of the vessel.

According to a second aspect, the invention relates to an arrangement for measuring the volume of liquid from a patient, the arrangement comprising a measuring vessel and a collection bag being connected by a hose connection according to the above described hose connection.

According to a third aspect, the invention relates to a use of an arrangement according to the second aspect for collection of urine from a patient.

According to a fourth aspect, the invention relates to a vessel for measuring volume of liquid, in particular urine from bedridden patients. The vessel comprises a hollowed member for receiving and containing the liquid, the bottom surface of the member having a curved shape provided on each side of an intermediate part defining a central column terminating in an outlet of the vessel.

The outlet can for example be an outlet defined by the first tubular member according to the connection as mentioned above, so that the vessel can be coupled to the bag by a hose connection as mentioned above (see FIGS. 7a+b).

The vessel is provided with a measuring scale indicating the volume of liquid present therein. As the bottom surface is curved, the scale can basically not be a linear scale, but in order to solve that, the vessel is provided with recesses or other elements taking up a predefined volume of the vessel, which makes it possible to use a linear scale on the vessel. The recesses can for example be provided on the backside of the vessel and defines a straight horizontal bottom surface inside the vessel at a level substantially equal to the level at which the curved surface begins.

The curved surface of the vessel allows for a better hygiene as there are no corners that can be difficult to access and clean from outside. Furthermore, the curved surface provides a more ergonomic vessel being easier to hold.

An embodiment of the vessel is shown in FIGS. 7a-8b.

According to a fifth aspect, the invention relates to an arrangement for measuring and collecting body liquids, the arrangement comprising a measuring vessel having at its top end a liquid inlet and at its lower end a liquid outlet provided with a valve and a liquid collection bag connected to the liquid outlet and suspended from the measuring vessel, a hollow valve body being placed in and vertically displaceable within the measuring vessel, and a part of the liquid outlet has the shape of a valve seat for the hollow valve body, the interior of the valve body being divided into a reception chamber and an overflow chamber, said reception chamber being connected to the liquid inlet and having at the lower end of the valve body at least one outlet opening which in the closed position of the valve body is closed by the valve seat and which at its upper part is connected to the measuring vessel through at least one hole in the chamber wall, and said overflow chamber having at its lower end a duct which is directly connected to the liquid outlet of the measuring vessel and which at its top end is connected to the measuring vessel via a hole in the chamber wall, the holes connecting the reception chamber to the measuring vessel and the measuring vessel to the overflow chamber being placed on the same side of the hollow valve body, and wherein the measuring vessel and collection bag is connected by a hose connection according to the first aspect of the invention.

The arrangement is further described below with reference to FIGS. 8a-9e.

DESCRIPTION OF THE FIGURES

Embodiments of the invention will now be described in details with reference to the accompanying figures, wherein FIGS. 1a-c show a first embodiment of a connection according to the invention, FIGS. 2a-c show a second embodiment of a connection according to the invention, FIGS. 4a-c show a fourth embodiment of a connection according to the invention, FIGS. 7a-b show a vessel according to the invention.

FIGS. 1a-c show a first embodiment of a connection comprising a first tubular member 1 defining an outlet 2 and having two oppositely arranged protrusions 3 provided on its outer surface. The first tubular member 1 forms part of a bottom part 4 of e.g. a vessel. A second tubular member 5 is adapted to be connected to the first tubular member 1 by sliding it over the first tubular member 1 so that the two oppositely arranged recesses 6 engage with the respective protrusion 3 as shown in FIG. 1b.

Figure 3C:
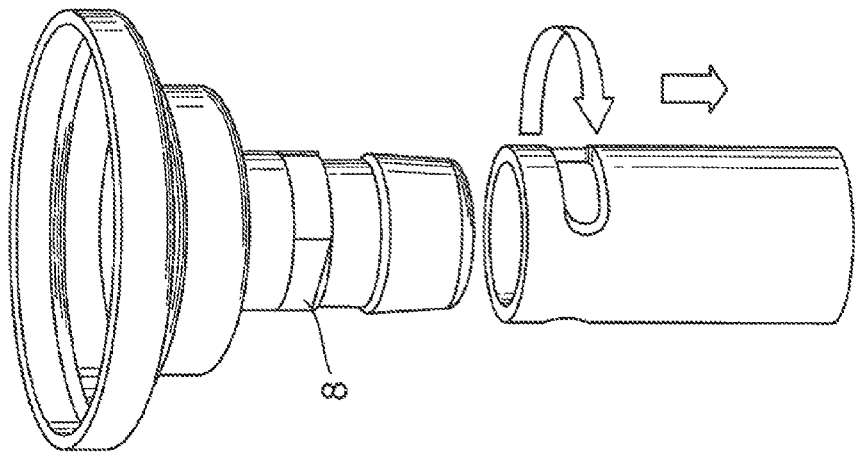
FIGS. 3a-c show a third embodiment of a connection according to the invention.

In order to separate the connection, the second tubular member 5 is turned and subsequently drawn downwards as shown in FIG. 1c so that the protrusions 3 disengage from the recesses 6.

As the second member 5 is preferably made of a soft plastic material, it may be compressed on the two sides opposite to the sides where the recesses 6 are provided, so that the sides comprising the recesses are widened and can disengage from the protrusions 3.

The protrusion 3 comprises an upper support surface at least partly formed as a ledge supporting a corresponding support surface of the recesses 6 of the second tubular member, so that the second tubular member 5 is positioned in a locked but separable connection with the first tubular member, as best shown in FIG. 1b. The support surface extends perpendicularly and radially out from the first tubular member thereby constituting the ledge. This ensures that the second tubular member does not come off by accident, as the support surface of the recess rest on the ledge of the protrusion 3. By use of this connection, it is easy to connect the two tubular members with each other without much energy needed, while still obtaining a safe locked connection due to the protrusions 3 and recesses 6. Furthermore, the connection is easily separable, as the second tubular member just need to be twisted or turned and pulled in order to disengage the protrusions 3 from the recesses 6. In other embodiments, indicated in FIGS. 10a-c, the easy separation or disconnection of the members is facilitated by providing either one, or both, of the tubular members with a ramp.

FIGS. 2a-c show another embodiment of the connection, wherein the protrusions 3 are formed as an arrow, the recesses 6 having a corresponding shape. The second tubular member 5 is connected to and separated from the first tubular member 1 in a similar way as the embodiment of FIGS. 1a-c.

The diameters d1, d2, d3 and d4 as referred to in the specification above are shown in FIG. 2a.

Figure 3B:
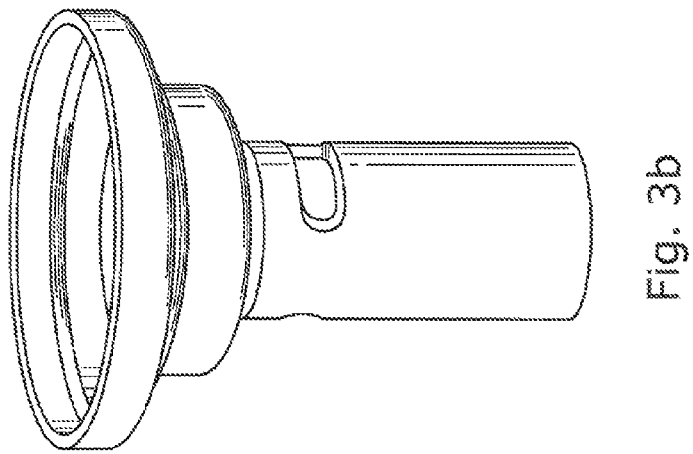
Figure 3A:
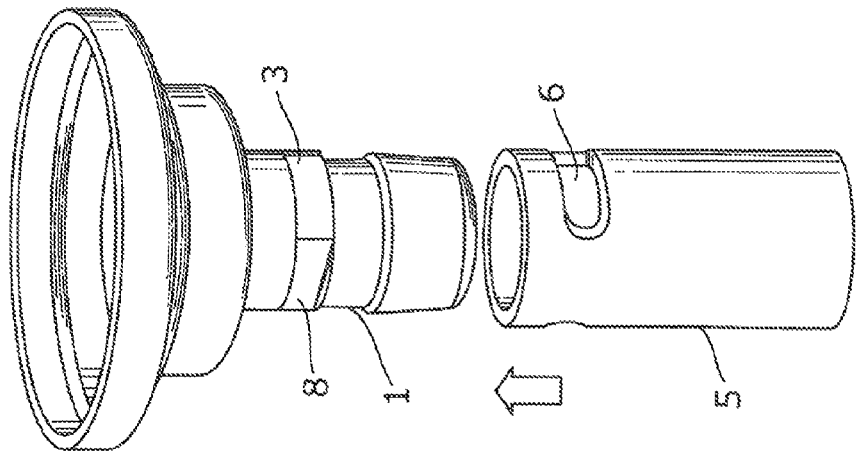

The second tubular member 5 is slotted along the line 7 to ease the mounting. FIGS. 3a-c show another embodiment of the connection having elongated protrusions 3 extending peripherally along the outer surface of the first tubular member 1. The second tubular member 5 is connected to and separated from the first tubular member 1 in a similar way as the embodiments of FIGS. 1a-2c.

Recesses 8 are provided in the outer surface of the first tubular member in order to ease the mounting, but can also be used as space for compressing the second tubular member 5 when separating it from the first tubular member 1.

FIGS. 4a-c show another embodiment of the connection according to the invention, wherein the second tubular member 5 is slid on and finally turned in order to connect it to the first tubular member 1. The first member 1 comprises a slot 9 providing an opening channel in the sidewall extending from an upper edge of the member to the recesses 3. The protrusions 3 are guided through the channel to obtain the engaged position in the recesses 6. The protrusions 3 and recesses 6 have corresponding slanting upper support surfaces for obtaining an even better connection not separating by accident.

Figure 5C:
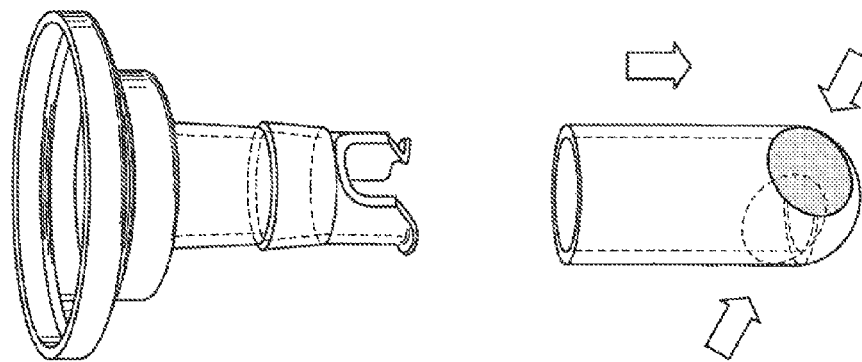
FIGS. 5a-c show a fifth embodiment of a connection according to the invention.
Figure 5B:
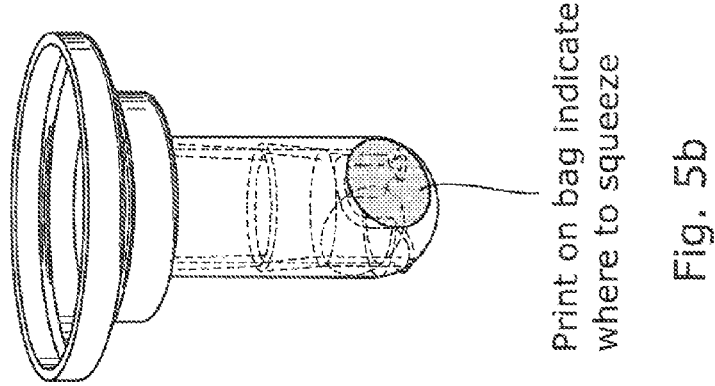
Figure 5A:
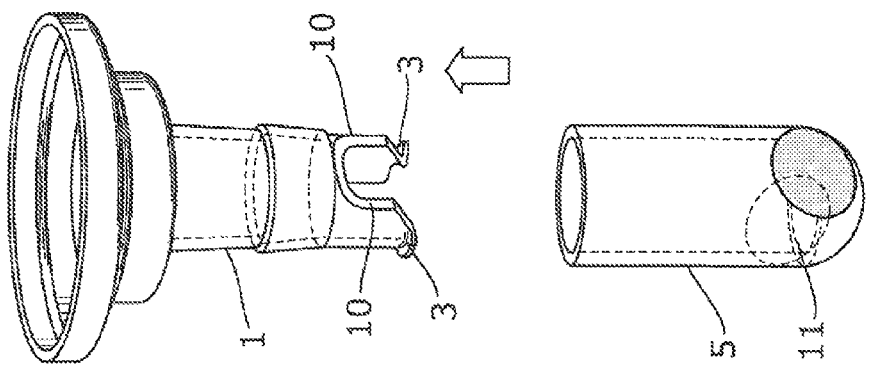

FIGS. 5a-c show another embodiment of the connection according to the invention, wherein the protrusions (barbs) 3 are provided at a distal end of the first tubular member 1 the protrusions 3 being adapted to engage a distal edge 11 of the second tubular member 5. The first tubular member 1 comprises two opposite flexible leg parts 10 each having a protrusion 3, the leg parts 10 being bendable towards each other for disengaging the protrusions 3 from the edges of the second tubular member 5. The second tubular member 5 may for example comprise prints showing where to squeeze the leg parts 10, as shown in FIG. 5b.

Thus, the second tubular member 5 is separated from the first tubular member 1 by squeezing the leg parts 1 towards each other and then drawing the member 5 downwards, as shown in FIG. 5c.

The outline of the protrusions and recesses shown in FIGS. 1a-5b are examples, which provide a proper locked separable hose connection, but other outlines may of course be used.

Figure 6:
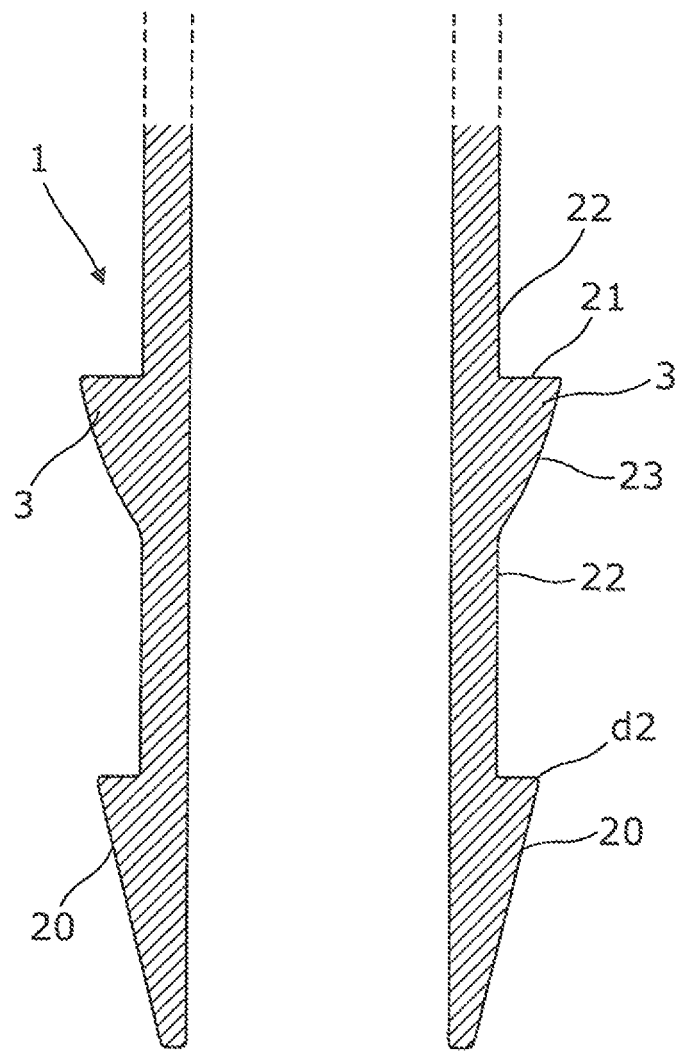
FIG. 6 shows a cross sectional view of a first tubular member according to the invention.

FIG. 6 shows a cross sectional view of a first tubular member 1 according to the invention. The member 1 comprises a widened conical portion 20 with a diameter d2 as shown in FIG. 2a and a protrusion 3. The protrusion 3 comprises a support surface 21 for a corresponding support surface of the recesses of a second tubular member, the support surface 21 extending substantially perpendicularly and radially out from the outer surface 22. An inclined surface 23 extends from the distal end of said support surface 21 towards the outer surface. The support surface 21 is shown in the form of a substantially even or plane ledge. The inclined surface 23 eases the sliding movement of a second tubular member over the protrusion 3 to obtain the locked but separable connection between the ledge on the first and the corresponding recess on the second tubular member.

Figure 7C:
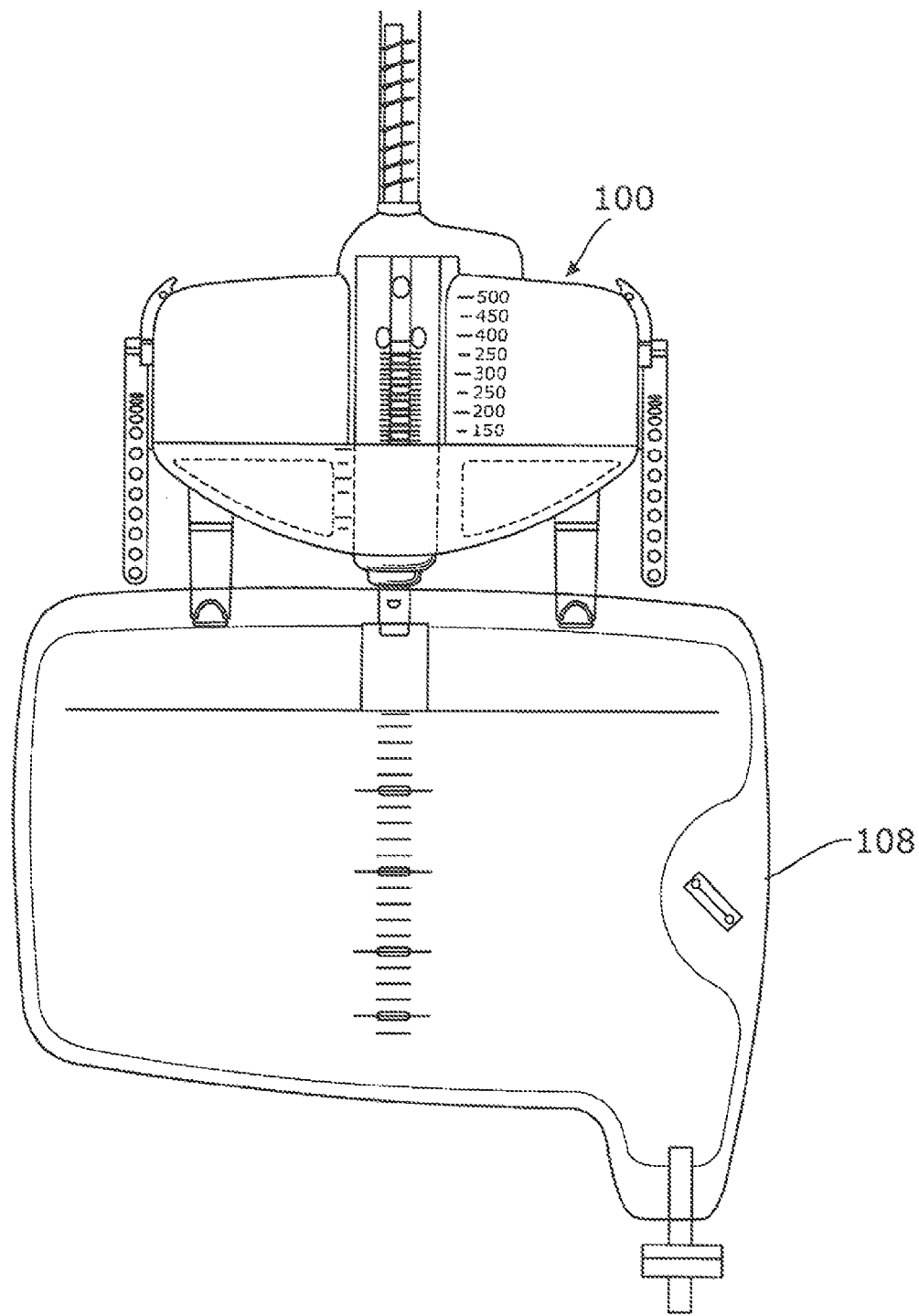
FIG. 7c shows a vessel and a collection bag connected by a hose connection according to the invention.

FIGS. 7a-b show a front and back view of a vessel according to the invention for measuring volume of liquid, in particular urine from bedridden patients. The vessel 100 comprises a hollowed member with an inlet 102 for receiving and containing the liquid, and wherein the bottom surface 103 has a curved shape. An outlet 104 is provided in the bottom of the vessel 100, which can be coupled to a collection bag as shown in FIG. 7c.

The vessel 100 is provided with a measuring scale 105 indicating the volume of liquid present therein. On the basis of a curved bottom surface 103, the measuring scale 105 can basically not be a linear scale, but in order to solve that problem, the vessel 100 is provided with filling elements 106 provided as recesses on its backside defining a straight horizontal bottom surface 107 at a level substantially equal to the level at which the curved surface begins. Due to the presence of the filling elements 106 taking up a predefined volume of the vessel and thereby compensating for the curved bottom surface 103, it is possible to use a linear scale 105.

The curved surface 103 of the vessel 100 allows for a better hygiene as there are no corners that can be difficult to access and clean from outside. Furthermore, it provides a more ergonomic vessel being easier to hold.

FIG. 7c shows a vessel 100 and a collection bag 108 connected to each other via the outlet 104 of the vessel and an inlet of the bag, which may be formed by a tubular member being adhered to the bag 108.

Figure 8A:
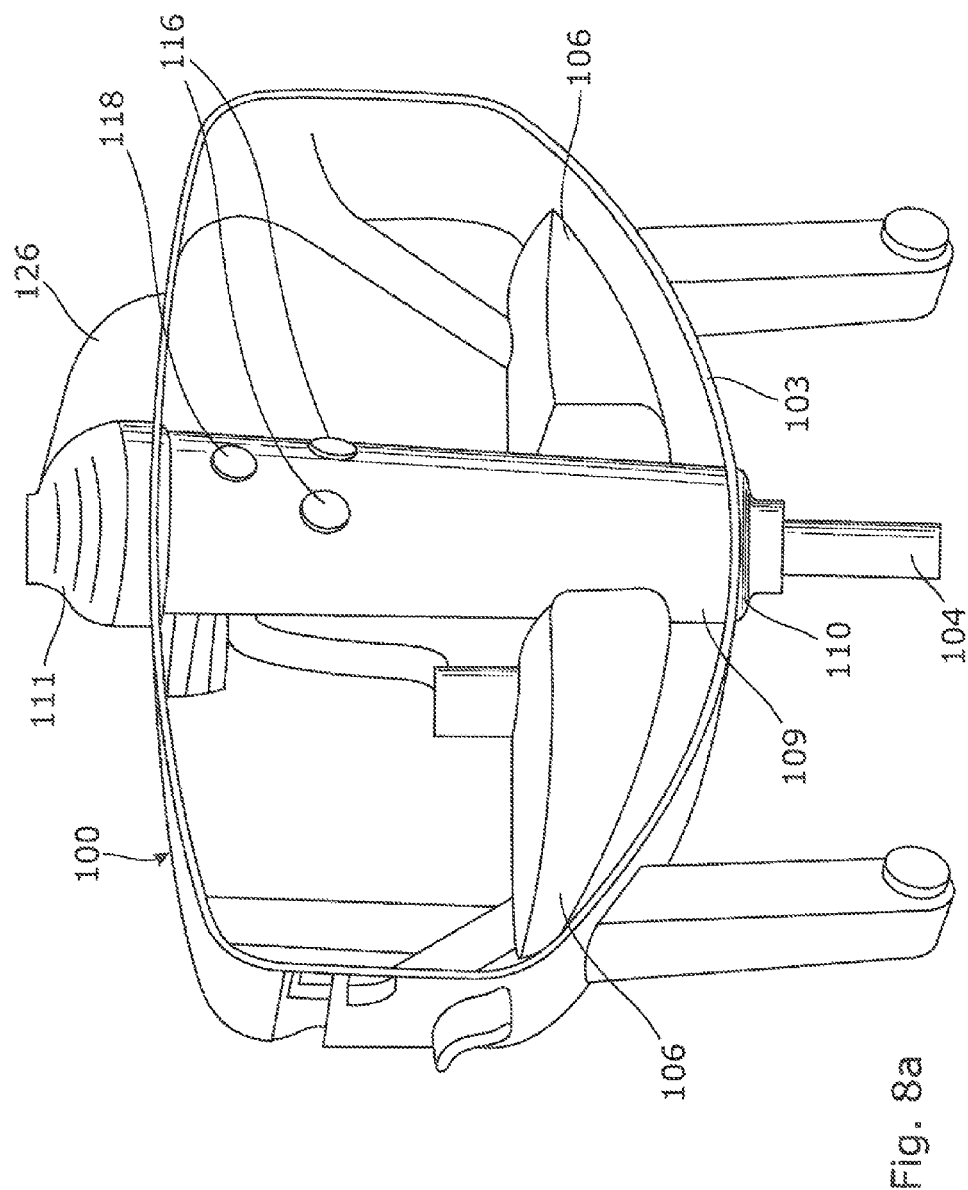
FIG. 8a-b show the vessel of FIGS. 7a-c more in detail.
Figure 8B:
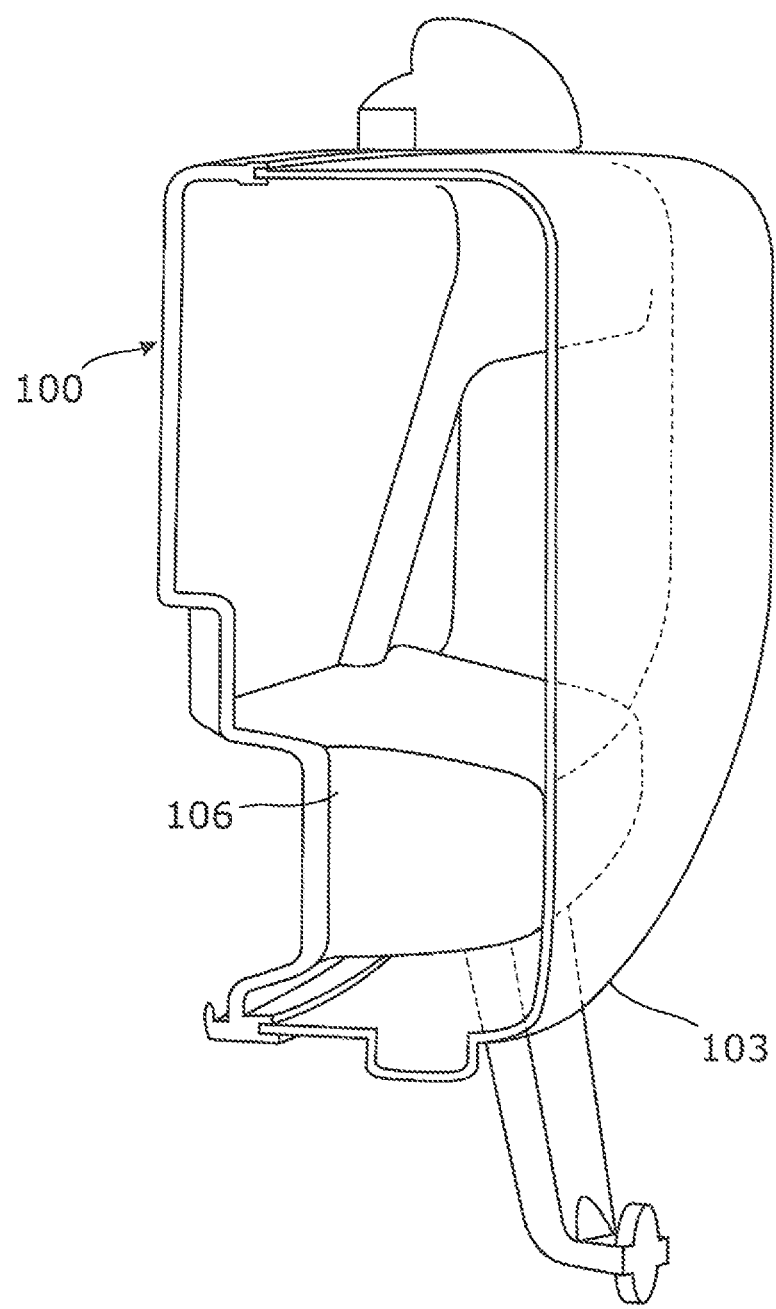

FIGS. 8a-b show transparent views of the vessel of FIGS. 7a-c in order to see the inside of the vessel more in detail. The vessel 100 comprises the hollowed member for receiving and containing the liquid, and the bottom surface 103 has a curved shape provided on each side of a central column terminating in the outlet 104 of the vessel 100. The central column defines a valve body 109 for the vessel, the valve body 109 being axially displaceable by rotation and which at its lower end is in contact with a valve seat 110 and is closed at the top with a cover 111. The valve body 109 is described more in detail with reference to FIGS. 9a-e.

FIG. 8b is a cross-sectional view of the vessel 100. As seen in FIG. 8b, the filling element 106 is provided as a projection moulded in the back wall of the vessel.

FIGS. 9a-e show sectional views of a valve body 109 of the vessel 100 as shown in FIGS. 7a-c and FIGS. 8a-b.

Figure 9A:
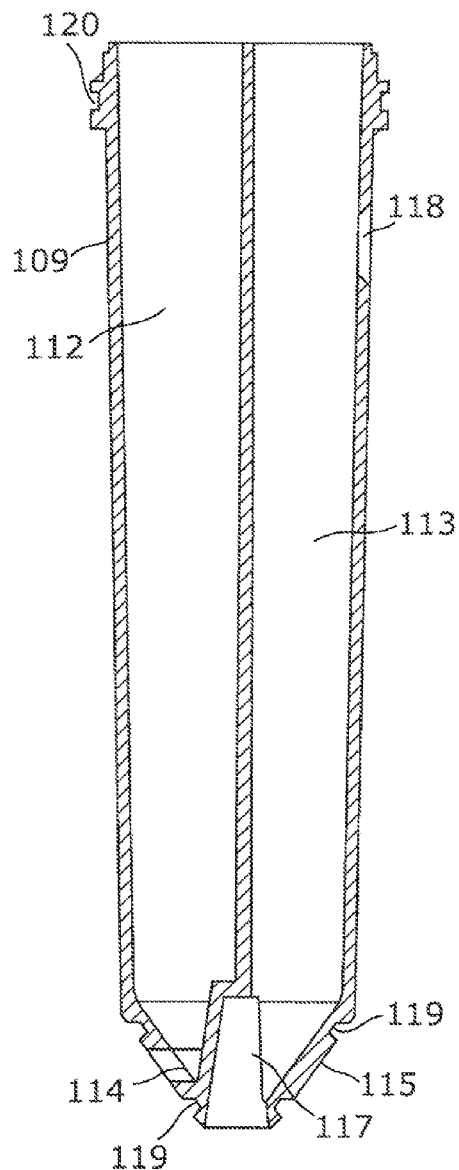
FIG. 9a-e show sectional views of the valve body of the vessel according to the invention.
Figure 9B:
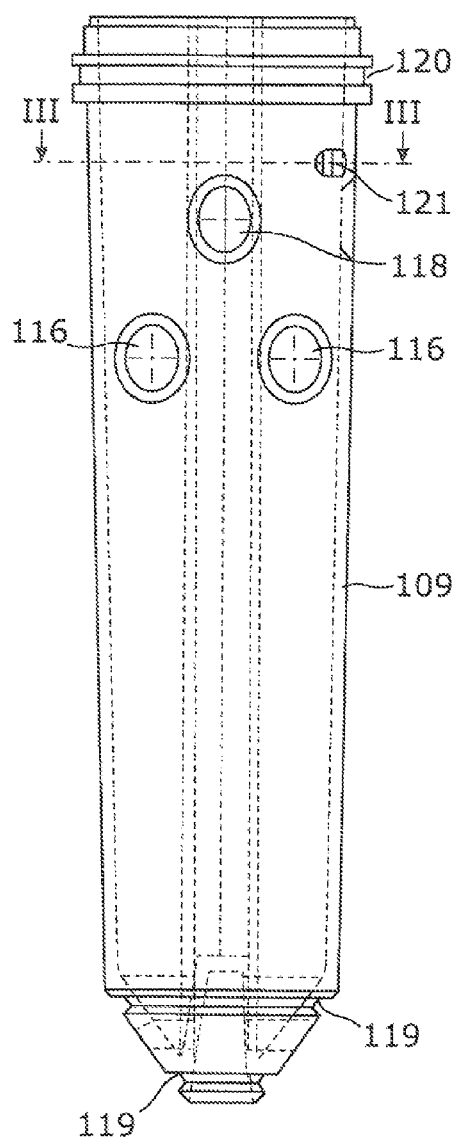
Figure 9C:
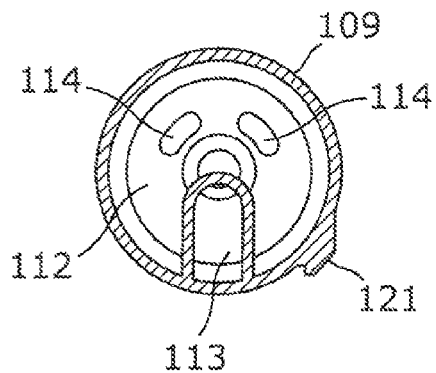
Figure 9D:
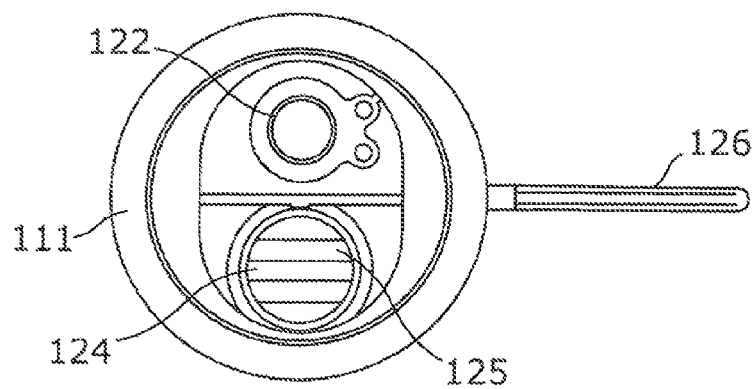
Figure 9E:
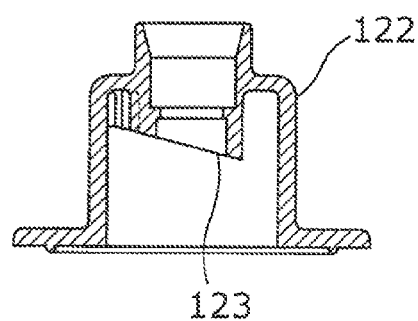

FIG. 9c is a sectional view along the line of the valve body of FIG. 9a, FIG. 9d shows the upper part of the valve body seen from the bottom, and FIG. 9e shows the upper part of the valve body of FIG. 9d in sectional view.

The central column defines the valve body 109, which is constructed with two chambers; a reception chamber 112 and an overflow chamber 113. At its lower end the reception chamber 112 is provided with two holes 114 ending in a valve surface 115 which contacts the valve seat 110 in its closed position thus preventing liquid outflow. At the upper end of the reception chamber 112 two holes 116 are provided in the wall separating the chamber 112 from the surrounding vessel 100.

At its lower end the overflow chamber 113 is provided with a duct 117 through which said overflow chamber 113 is in direct contact with the liquid outlet of the vessel. The liquid outlet is defined by a tubular member so that the vessel can be connected to a collection bag 108.

At the top end of the overflow chamber 113 a hole 118 is provided in the valve wall.

Two annular-shaped grooves 119 each comprising an O-ring (not shown) are provided on the outside of the valve body at the lower end thereof. An annular groove 120 comprising an O-ring (not shown) is provided.

The outside of the valve body 109 is also provided with a projection 121 being inserted in a helical groove formed on the outside of the back wall of the measuring vessel 100.

The cover 111 of the valve body 109 is provided with two openings one being a tubular member 122 ending in an inclined surface 123 covered by a rubber flap (not shown) permitting the introduction of liquid and preventing back flow of the same. A ventilation opening 124 is provided which is partially covered by support ribs 125 supporting an air filter (not shown).

The liquid passes down into the reception chamber 112 inside the valve body 109 via the tubular member 122. In its initial (closed) position the valve surface 115 of the valve body 109 is in contact with the valve seat 110 and consequently no liquid is allowed to pass through the holes 114. Therefore, the liquid level in the reception chamber 112 will rise and using the measuring scale 105a (see FIG. 7a) on the valve body 109, the volume of the collected liquid may be read.

When the liquid surface has reached the level of the holes 116, the introduction of additional liquid will start filling of the vessel 100.

The vessel is provided with an additional non-linear measuring scale 105b (see FIG. 7a) in the lower end of the vessel with the curved bottom surface to measure a first amount of liquid entering the vessel from the reception chamber. Due to the presence of the filling elements 106 compensating for the curved bottom surface, the measuring scale goes from the non-linear scale 105b to the linear scale 105.

If additional amounts of liquid are introduced the vessel 100 is also filled and through the hole 118 an overflow of liquid from the vessel 100 in the overflow chamber 113 may occur. From here the liquid passes via a duct 117 down through the liquid outlet 106 and into a collection bag 108.

At this time or at any earlier desired time the reception chamber 112 as well as the vessel 100 may be emptied by clockwise rotation of the wing 126. Such rotation causes the valve body 109 to be rotated and because the projection 121 is located in an upwards slanting groove (not shown) the valve body 109 is lifted upwards in connection with the rotation thus removing the valve surface 115 from the valve seat 110. Hence it is possible to empty the reception chamber quickly through the holes 114 and the vessel 100 through the space between the valve surface 115 and the valve seat 110 as liquid flows down into the collection bag 108 being connected to the outlet.

Figure 10A:
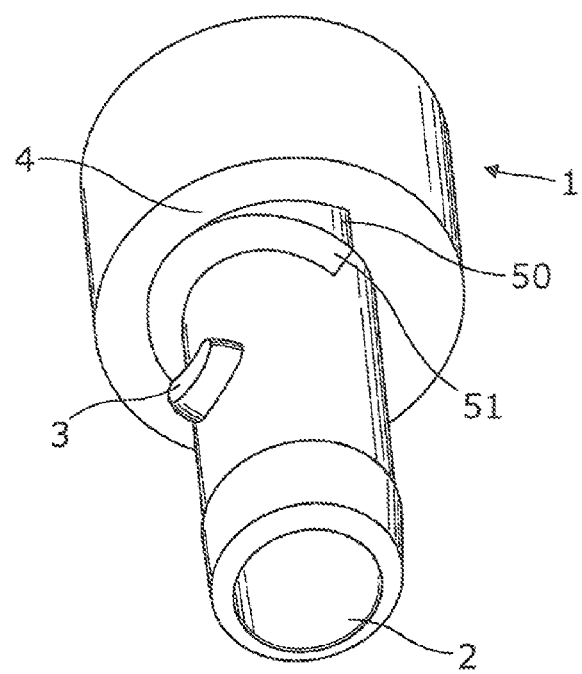
FIG. 10a-c show schematic, perspective views of a first tubular member having a semicircular section provided with a ramp according to the invention.
Figure 10B:
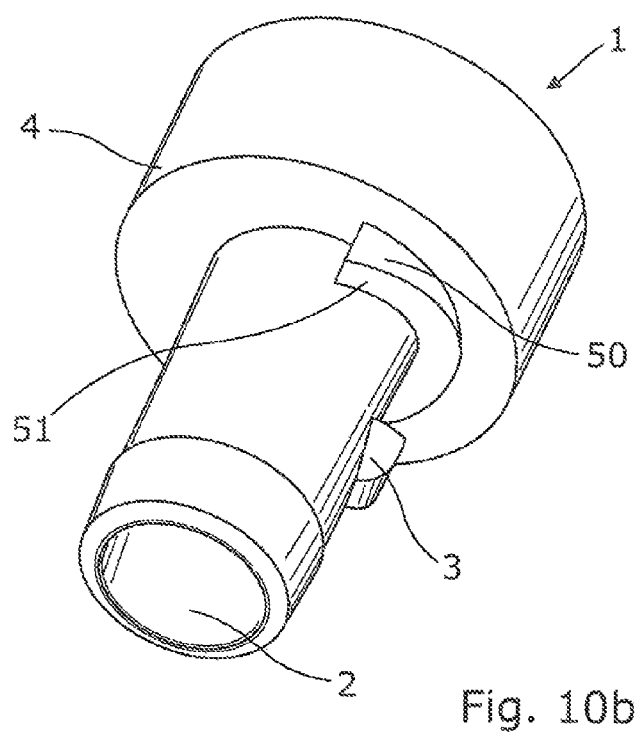
Figure 10C:
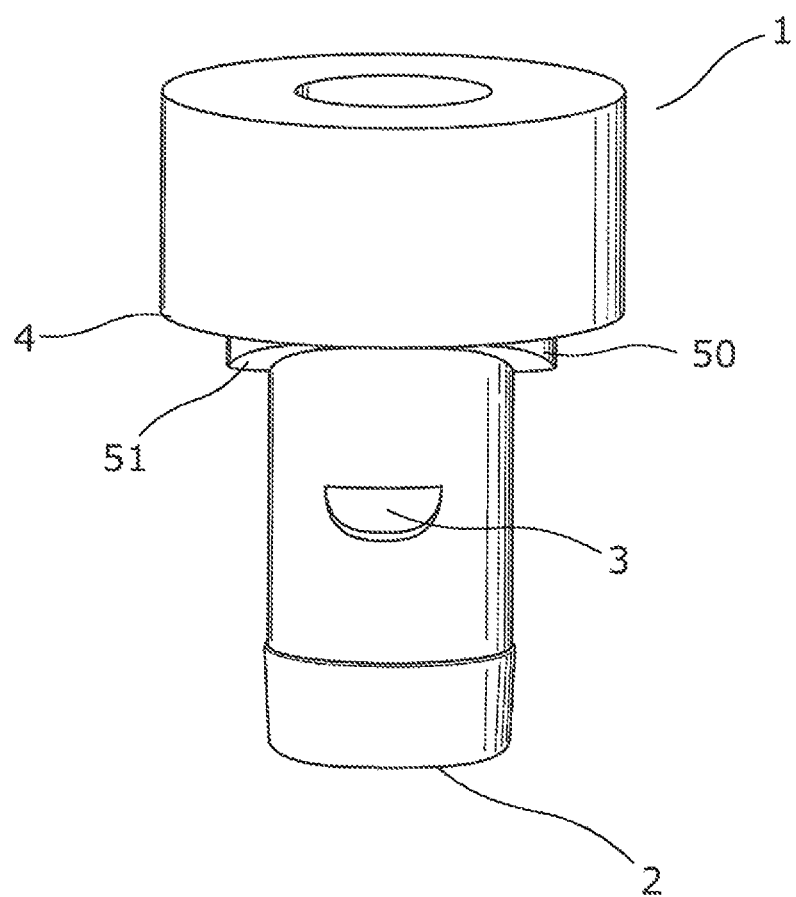

FIGS. 10a-c show embodiments of a first tubular member 1 defining an outlet 2 and having a protrusion 3 provided on its outer surface. The first tubular member 1 forms part of a bottom part 4 of e.g. a vessel as described above. A semicircular section 50 partly encircles the first tubular member shown adjacent to the bottom part 4. Section 50 forms a ramp

51 having a surface for engaging with an engaging surface of the second tubular member (not shown), the surface being substantially level with the bottom part 4 at a position e.g. above the protrusion 3 and "climbing" to a level distanced from the bottom part 4 at opposite positions of the outer surface of the first tubular member 1. The semicircular section can also be level with the bottom part 4 at any other suitable position around the tubular member.

The invention claimed is:

1. A hose connection for an arrangement for collection of liquid from a patient comprising;
   a first tubular member adapted to be in fluid connection with an organ of the patient and having one or more protrusions arranged on an outer surface said protrusions comprising a support surface at least partly formed as a ledge, and an outlet;
   a second tubular member being connected to a collection bag having an inlet to be connected to said outlet for collection of liquid coming through said first tubular member, the second tubular member being adapted to receive and surround at least a part of said first tubular member, the second tubular member having one or more recesses or edges being engageable with said protrusions, respectively, for providing a locked separable connection between the first and second tubular member;
   wherein the first tubular member further comprises a ramp positioned above the one or more protrusions and adapted to engage with a surface on the second tubular member, the ramp spirally extending around the first tubular member and toward the one or more protrusions such that rotation of the second tubular member relative to the first tubular member facilitates disengagement of the first and second tubular members.

2. The hose connection according to claim 1, wherein the support surface extends perpendicularly and radially out from the outer surface and wherein an inclined surface extends from the distal end of said support surface towards the outer surface.

3. The hose connection according to claim 2, wherein the inclined surface has a convex form.

4. The hose connection according to claim 1, wherein the one or more recesses or edges goes through the sidewall of the second member and has an outline substantially identical to the outline of the one or more protrusions.

5. The hose connection according to claim 1, wherein the first tubular member is substantially conical with an outer diameter (d3) near the outlet being smaller than an outer diameter (d1) upstream thereof.

6. The hose connection according to claim 5, wherein an inner diameter (d4) of the second tubular member is larger than the outer diameters (d1) and (d3) of the first tubular member.

7. The hose connection according to claim 1, wherein the first and second tubular members are adapted to be connected by pushing or turning the second tubular member over the first tubular member until the protrusion(s) one or more protrusions engages the recess(es) one or more recesses or edges.

8. The hose connection according to claim 1, wherein the one or more protrusions and one or more recesses or edges are adapted to be disengaged by compressing or turning the second tubular member.

9. The hose connection according to claim 1, wherein the first tubular member is made of a hard plastic material.

10. The hose connection according to claim 1, wherein the second tubular member is made of a soft plastic material.

11. The hose connection according to claim 1, wherein the first tubular member comprises two protrusions arranged diametrically opposite.

12. The hose connection according to claim 1, wherein said ramp is at least partly formed by a semicircular section on the first tubular member.

13. The hose connection according to claim 1, wherein said ramp is at least partly formed by an annular section on the first tubular member.

* * * * *